United States Patent [19]
Marcon

[11] Patent Number: 6,102,050
[45] Date of Patent: Aug. 15, 2000

[54] REMEDIAL DENTAL FLOSS

[76] Inventor: Robert Victor Marcon, 3471 Sinnicks Avenue, N. Falls Ont., Canada, L2J 2G6

[21] Appl. No.: 09/112,863

[22] Filed: Jul. 9, 1998

Related U.S. Application Data

[60] Provisional application No. 60/052,167, Jul. 10, 1997.

[51] Int. Cl.[7] ............................. A61C 15/00; A61K 7/26; A61K 7/18
[52] U.S. Cl. ........................ 132/321; 132/329; 132/323; 424/58; 424/52
[58] Field of Search ..................... 132/324, 321, 132/323, 329, 326, 327, 328; 424/58, 52, 48

[56] References Cited

U.S. PATENT DOCUMENTS

| | | | |
|---|---|---|---|
| 3,830,246 | 8/1974 | Gillings | 132/89 |
| 4,817,643 | 4/1989 | Olson | 132/329 |
| 4,952,392 | 8/1990 | Thame | 424/58 |
| 4,986,288 | 1/1991 | Kent et al. | 132/321 |
| 4,996,056 | 2/1991 | Blass | 424/443 |
| 5,033,488 | 7/1991 | Curtis et al. | 132/321 |
| 5,374,417 | 12/1994 | Norfleet et al. | 424/49 |
| 5,526,831 | 6/1996 | Gilligan et al. | 132/321 |
| 5,711,935 | 1/1998 | Hill et al. | 424/49 |
| 5,755,243 | 5/1998 | Roberts et al. | 132/321 |

*Primary Examiner*—John J. Wilson
*Assistant Examiner*—Robyn Doan

[57] ABSTRACT

The present invention relates to a remedial dental floss comprising a dental floss and titanium dioxide particles of 6.0 microns or less. Depending upon the structure, formulation, and final effects desired a binder may also be used to attach, adhere or otherwise incorporate particles of titanium dioxide and other substances onto or into the dental floss. In order to provide various other qualities one or more other ingredients, compounds or substances such as fluorides, peroxide based compounds, abrading agents, other pigmenting agents, sweeteners, and flavoring agents may also be incorporated into or utilized by the remedial dental floss disclosed herein. Regular use of such a remedial dental floss will significantly reduce the interproximal staining and discolorment of dental surfaces as well as providing all other benefits normally associated with flossing in a way that is convenient, inexpensive, and safe.

20 Claims, No Drawings

REMEDIAL DENTAL FLOSS

CROSS-REFERENCE

This application claims priority from U.S.A. Provisional Application, Ser. No. 60/052,167, filed Jul. 10, 1997.

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

This invention relates to dental flosses and, specifically, to remedial dental flosses which reduce dental decay and whiten teeth.

It is generally recognized by the dental profession that plaques, including those that are found between the interproximal surfaces of teeth, are a major cause of both dental decay and inflammatory periodontal disease. These plaques, which can contain 250 or more separate microbial species, use sugars and other fermentable carbohydrates to produce polymers which bind the organisms to the tooth surface and acids which cause its demineralization. In the first stages a carious lesion does not contain an actual cavity but with prolonged and repeated demineralization by the plaque created acids a cavity will form. Thus, each time something sweet is consumed plaques can produce at least 20 minutes of acid in the mouth which, in turn, seriously contributes to dental demineralization.

Furthermore, plaques, if not removed will in time form calculus, and calculus, is the mineralized bacterial plaque deposits found on the teeth or other solid oral structures such as restorations. Invariably, calculus is covered by a film of plaque, the organisms of which also occupy its porous structure. Its composition is generally made up of seventy percent organic salts and thirty percent micro-organisms and organic material. Moreover, its formation is always preceded by plaque accumulation which serves as an organic matrix for the subsequent mineralization of the deposit. Mineralization, by precipitation of mineral salts in plaque can start at any time from the second to the fourteenth day of plaque formation, but some individuals can begin to calcify plaque in four to eight hours. Initially, small crystals develop close to bacteria; gradually the intermicrobial matrix becomes entirely calcified and eventually the bacteria also become mineralized. Consequently, the presence of calculus not only makes effective oral hygiene impossible but can also seriously irritate gum tissues. Thus, its prevention and or removal to help control the inception or progression of inflammatory periodontal disease is of great importance.

As a result, dental professionals now highly recommend flossing, in addition to the conventional practice of using a brush and dentifrice, for flossing clears the interproximal surfaces of the teeth in a manner that a toothbrush, with or without a dentifrice, cannot achieve. With this two step cleaning method effective oral hygiene is greatly improved.

In addition to the various problems created by plaques consumers have always desired the cosmetic beauty of white shiny teeth. However, the stains and discolorment found in and around the interproximal surfaces of teeth are not only difficult to remove but are also difficult to prevent. Treatments for this condition are, however, only available from professional dental practitioners, certain dentifrices, and some mouthwashes. Unfortunately, professional dental practitioners are invariably expensive, time consuming, and not always effective, whereas, a brush and dentifrice alone are ineffective in cleaning, let alone actually whitening, the interproximal surfaces of teeth. Mouthwashes have been suggested by the prior art but as yet no commercial products have been realized that can efficiently clean or whiten these interproximal dental surfaces. As a result, there is presently a very great need in the general public for a convenient, effective, and inexpensive solution to not only help whiten interproximal dental surfaces but to also maintain this whiteness for an extended time period.

With these thoughts in mind it becomes self-evident that there is a large deficiency with contemporary dental flosses in providing satisfactory remedies to the aforedescribed problems. In consequence, the invention detailed within this disclosure can provide a more effective and optimal solution than can be currently achieved.

OBJECTS AND ADVANTAGES

The invention disclosed herein overcomes many of the drawbacks listed in the prior art while also providing a more effective solution and improved performance over presently used dental flosses.

In addition, some of the objects and advantages associated with this invention, or its various versions, are described below. Others will become apparent as the description proceeds.

OBJECTS (1) To help reduce the various dental problems caused by oral plaques.

(2) To help maintain the natural whiteness of the interproximal surfaces of teeth.

ADVANTAGES (1) The remedial dental floss disclosed herein utilizes extremely small titanium dioxide particles which can be absorbed by the enamel of the teeth. The result provides not only extended whiteness but a smooth finish that resists discolouration and attack.

(2) The delivery of the titanium dioxide particles to the interproximal surfaces and subgingival areas of the teeth is superior to any other dental floss, brush and dentifrice or mouthwash presently available.

(3) Fluoride based compounds may be used within the remedial dental floss to significantly reduce the incidence of dental decay.

(4) In addition to pigmenting the enamel surfaces of teeth, titanium dioxide can be used as a mild abrading agent to help clean dental surfaces. Cleaner dental surfaces will, in turn, not only reduce dental decay but will also increase the effectiveness of pigmenting agents as well as other medicaments such as fluorides.

(5) Professional dental personnel are not required. This not only reduces time but cost as well.

(6) The ingredients employed by the remedial dental floss of this disclosure are cost competitive.

(7) The cost and mechanics of incorporating into the remedial dental floss the various ingredients disclosed herein are both inexpensive and technically favourable.

SUMMARY OF THE INVENTION

The invention disclosed herein details a remedial dental floss which can be utilized in reducing the effects produced by dental plaques and improving the whiteness of teeth. To begin, dental plaques, which can contain 250 or more separate microbial species, use sugars and other fermentable carbohydrates to produce polymers which binds them to the tooth surface and acids which cause dental demineralization. In time, these plaques will produce caries and form calculus. The establishment of calculus can seriously irritate gum tissues and so promote the advance of periodontal disease. Do to its porous structure calculus can also harbour a multitude of bacterial plaques and so promote its continued spread. This makes effective oral hygiene impossible. Dental plaques are also capable of producing various offensive odours which, while not harmful, are selfevident in their undesirability.

In addition to the various problems created by plaques consumers have always desired the cosmetic beauty of white shiny teeth. However, the stains and discolorment found in and around the interproximal surfaces of teeth are not only difficult to remove but are also difficult to prevent. Treatments for this condition are, however, only available from professional dental practitioners, certain dentifrices, and some mouthwashes. Unfortunately, professional dental practitioners are invariably expensive, time consuming, and not always effective, whereas, a brush and dentifrice alone are ineffective in cleaning, let alone actually whitening, the interproximal surfaces of teeth. Mouthwashes have been suggested by the prior art but as yet no commercial products have been realized that can efficiently clean or whiten these dental surfaces.

In response to these problems, the invention disclosed herein utilizes a remedial dental floss so that the consumer can, when flossing, administer various highly effective ingredients or compounds to the interproximal surfaces and subgingival areas of the teeth. Depending upon the final design selected these compounds can be used, with or without binders, but in all cases herein disclosed they must include minute particles of titanium dioxide in order to properly clean and whiten teeth. Fluorides can also be employed to reduce dental decay as can peroxide based compounds. Various other ingredients or compounds such as other pigmenting agents, abrading agents, sweeteners, and flavouring agents can also be utilized accordingly.

As a result, a remedial dental floss can render many benefits. It can diminish dental plaques and other related dental diseases. Cosmetically, teeth will tend to be whiter and appear healthier and, in final summation, all of this can be accomplished effectively, conveniently, inexpensively, and safely.

BRIEF DESCRIPTION OF THE DRAWINGS

Not applicable.

DETAILED DESCRIPTION OF THE INVENTION

The present invention pertains to a remedial dental floss which can be used to help reduce the incidence of or the effects associated with one or more of the following manifestations:

(1) Dental plaques.
(2) Stains and discolorment found in and around the interproximal surfaces of teeth.

While these objectives are obviously desirable they are achieved in a most unique and novel manner by including, in the remedial dental floss, various specialized ingredients. These ingredients can work alone or in conjunction with others but in all cases herein disclosed the remedial dental floss shall utilize a dental floss and titanium dioxide particles. While a floss with titanium dioxide is mandatory the other ingredients listed below are not and, thus, only those required to make the remedial dental floss desired need be added. As a result, a remedial dental floss when utilized in its various forms can provide the consumer with many benefits some of which are listed below:

(1) The remedial dental floss disclosed herein utilizes extremely small titanium dioxide particles which can be absorbed by the enamel of the teeth. The result provides not only extended whiteness but a smooth finish that resists discolouration and attack.
(2) The delivery of the titanium dioxide particles to the interproximal surfaces and subgingival areas of the teeth is superior to any other dental floss, brush and dentifrice or mouthwash presently available.
(3) Fluoride based compounds may be used within the remedial dental floss to significantly reduce the incidence of dental decay.
(4) In addition to pigmenting the enamel surfaces of teeth, titanium dioxide can be used as a mild abrading agent to help clean dental surfaces. Cleaner dental surfaces will, in turn, not only reduce dental decay but will also increase the effectiveness of pigmenting agents as well as other medicaments such as fluorides.
(5) Professional dental personnel are not required. This not only reduces time but cost as well.
(6) The ingredients employed by the remedial dental floss of this disclosure are cost competitive.
(7) The cost and mechanics of incorporating into the remedial dental floss the various ingredients disclosed herein are both inexpensive and technically favourable.

The disclosure will now describe the remedial dental floss in detail. It will first begin by reporting the basic or root structure of the remedial dental floss and then progress to reveal other components, ingredients, and compounds which can be used to achieve various other results.

Thus, the remedial dental floss of the present invention begins with a basic or root structure which comprises at least one suitable or commercially available dental floss, titanium dioxide, and when needed or required, at least one suitable or commercially available binder. These three components will now be detailed individually below.

Dental Flosses

The meaning of the words, "dental floss", used herein by this disclosure, includes both dental flosses and dental tapes, and any other similar article. Moreover, the dental flosses and tapes used in the present invention can include any suitable or commercially available dental floss or tape. The flosses and tapes used herein can also be fabricated from either natural or synthetic sources examples of which include, but are not limited to, filaments or yarns of high and normal tenacity polymers, nylon, rayon, dacron, acrylic, acetate polymers, polypropylene, polyethylene, and other plastics alone or in combination. Natural substances may include, but not limited to, cotton, wool, silk, linen, and other staple fibres alone or in combination. Blends of synthetic-natural fibres can also be used. However, synthetic filaments are preferred for they are more durable, generally less expensive, and easier to work and procured.

The length, diameter, structure or design of the floss itself is also not limited to any specific size, shape, arrangement or configuration and thus, can be fabricated to suite any specific intention. It can, for example, be composed of a plurality of individual filaments that have been formed together to give a larger thread having a sufficiently small diameter to permit insertion between the teeth. It can also comprise a composite multifilament yarn bonded to an extruded monofilament or to another multifilament yarn. A single monofilament thread is also useful. Other suitable variations are also well known in the art and as such are also useable in the invention disclosed herein.

Pigmenting Agents

The remedial dental floss will use titanium dioxide in order to whiten and maintain the whiteness of teeth. In this task the pigmenting agent titanium dioxide is particularly useful because of its brilliant opaque white colour and its extremely small particle size. Though a larger size may be used the titanium dioxide particles most useful in the present remedial dental floss has an approximate size of between 1.5 and 0.1 microns and most preferably has a particle size between 0.2 and 0.1 microns. A titanium dioxide particle having this approximate size allows it to be absorbed by the enamel of the teeth and so occupy the space between the hydroxyapatite crystals or prisms that make up the enamel layer of the teeth. Thus, this particle competes with the substances that tend to attack, stain or discolour teeth by filling the space between the prisms with an inert white material instead of an undesirable substance or colouring. A further benefit of titanium dioxide as the pigmenting agent is its ability to also function as a mild polishing or abrading agent when it is being used.

The remedial dental floss may also make use of one or more other colouring or pigmenting agents. These pigmenting agents may be obtained from either natural or synthetic sources, or a combination thereof. Thus, by way of example and not limitation, some common available colouring agents may include FD and C-type dyes and lakes, fruit and vegetable extracts, and other similar substances. Suitable pigmenting agents may also be used to colour the filaments or fibres comprising the floss as a means of producing a decorative effect or as a means of signifying or designating certain formulations.

The incorporation of titanium dioxide into the remedial dental floss can be relatively straight forward. It can, for instance, be mixed with an aqueous or other suitable medium and then applied to a dental floss. Alternately, it can be mixed with an aqueous or other suitable medium and then blended into a binder or just blended into a binder without using an aqueous substance at all. In addition, titanium dioxide as well as other substances used herein can be encapsulated or microcoated in order to protect then from unwanted contamination or reactions until used or to prolong their useful shelf life. Suitable encapsulating materials may include, but are not limited to, methyl cellulose, sodium carboxymethyl cellulose, ethylcellulose, and other coating polymers or materials which can coat and preserve an ingredient until released by the mechanical action of flossing or the usual enzymatic action provided by saliva.

While titanium dioxide can be used alone or in combination with other substances the actual quantity used will inevitably depend to a large extent on the other types of substances used, the formulation of the binders, the type of dental flosses used, and the final effects desired. As a result, the amount or quantity used is given great latitude. For instance, a minimal amount of binder can be used to attach a very large quantity of titanium dioxide to the dental floss. Similarly, titanium dioxide can be blended, mixed or otherwise incorporated into a polyethylene glycol wax, microcrystalline wax or other suitable binder with the resulting composition then applied to dental floss in a conventional manner. Alternately, the amount of binder can also be increased so as to vary the frictional coefficient of floss. In still another example a floss, constructed from either a synthetic material, a natural material, a synthetic-natural blend or other liquid absorbing floss can be soaked in a bath of liquified or wetted titanium dioxide particles in order to impregnate and or coat it. The impregnated and or coated floss can then be used as is or left to dry. In such cases a binder is not at all required, thus maximizing the amount of titanium dioxide used. In yet another example the formulation uses other ingredients to achieve various other effects. Such ingredients can include fluorides, peroxide compounds, abrading agents, other pigmenting agents, sweetening agents, and flavouring agents. Consequently, with such a wide and diverse use of ingredients and components exact quantitative values are impractical. However, the amount of titanium dioxide as well as all other components or ingredients used herein, must always be of a safe and non-toxic quantity.

In addition to the aforedescribed methods the integration of titanium dioxide particles into a remedial dental floss can still be accomplished in numerous other fashions. Some of these methods as well as other information regarding compositions, ingredients, components, and techniques are also detailed in the patents disclosed below. These patents, the entire contents of which are hereby incorporated by reference into this specification, are but a small sampling of the information currently available in the art and which may also be used or employed herein by this disclosure.

(1) U.S. Pat. No. 5,573,850 Invented by: David V. Cunningham, Sheldon Kavesh, and Christopher P. Griffin. Issued: Nov. 12, 1996

(2) U.S. Pat. No. 5,560,377 Invented by: Marion Donovan. Issued: Oct. 1, 1996

(3) U.S. Pat. No. 5,526,831 Invented by: Sean G. Gilligan, Dermot T. Freeman, Larry J. Oliphant, Jeffrey S. Meessmann, Patrick J. Hanley, and Gerald S. Szczech. Issued: Jun. 18, 1996

(4) U.S. Pat. No. 5,423,337 Invented by: Gary Ahlert. Issued: Jun. 13, 1995

(5) U.S. Pat. No. 5,357,990 Invented by: Christopher H. Suhonen, and John A. Kaminski. Issued: Oct. 25, 1994

(6) U.S. Pat. No. 5,353,820 Invented by: Christopher H. Suhonen, and Pedro L. Jusino. Issued: Oct. 11, 1994

(7) U.S. Pat. No. 5,220,932 Invented by: Jacob M. Blass. Issued: Jun. 22, 1993

(8) U.S. Pat. No. 5,209,251 Invented by: John P. Curtis, and James H. Kemp. Issued: May 11, 1993

(9) U.S. Pat. No. 5,098,711 Invented by: Ira Hill, and Robert D. White. Issued: Mar. 24, 1992

(10) U.S. Pat. No. 4,548,219 Invented by: Michael G. Newman. Issued: Oct. 22, 1985

Binders

Binders are used in the invention disclosed herein to bind or otherwise attach to the dental floss the pigmenting agent titanium dioxide and various other medicaments or compounds herein specified by this disclosure. They also provide the ability to alter the frictional characteristics of the floss as well as help bind together the individual filaments comprising the dental floss itself. Moreover, the varieties used herein are not restricted to any specific types or compositions and are thus, given great freedom in their formulations, structures or make-ups. Examples of some suitable binders may, therefore, include, but are not limited to, natural waxes from insects, animals or plants, synthetic waxes, petroleum waxes such as polyethylene glycol wax, microcrystalline wax, liquid polyethylene glycol esters of beeswax as well as other water soluble or non-water soluble wax or wax-like compounds, or water soluble or non-water soluble polymers, soaps, gums, resins, and other substances known in the art. It must also be remembered that the edicts of safety and non-toxicity must be absolutely observed for binders as well as all other ingredients that may be used in the construction, composition, or formulation of the remedial dental flosses disclosed herein.

The aforedisclosed information has so far detailed the basic or root structure of the remedial dental floss. However, the disclosure will now detail other ingredients which can be used to provide various other results. These ingredients can be added to the root structure of the remedial dental floss alone or in combination with others. Their individual procurement may also be derived, where possible, from either natural or synthetic sources or a combination thereof.

Fluorides

Another substance which the remedial dental floss may utilize is a fluoride based compound. These compounds, also called fluorides, have in the past been found to help prevent the incidence of carious lesions or caries. Caries are caused when teeth demineralize at a rate faster than they remineralize and most demineralization is caused by acid producing dental plaques. Remineralization, however, is promoted by calcium and phosphate and these elements are the chief remineralizing agents found in saliva. Fluoride based compounds, therefore, provide protection from carious lesions or caries by acting as a catalyst to speed the precipitation of calcium phosphate, in the form of a hydroxy apatite, onto or into teeth. However, this is not fluoride's only role. It is also able to inhibit the activity of some bacterial enzymes and their acid producing processes, and at extremely high concentrations it can also kill some plaque bacteria. Even more important, it tends to become incorporated into the apatite, as a fluoridated hydroxy apatite, or "fluorapatite", creating a mineral that is appreciably less dissolvable by acid.

Hence, the remedial dental floss detailed herein may contain one or more fluoride based compounds. Their assimilation into the remedial dental floss can be likened to, but are not limited to, that used by titanium dioxide. The fluoride compounds used may also be slightly soluble in water or may be fully water soluble. They are, however, foremost characterized by their ability to release fluoride ions in water and by freedom from undesired reaction with the other compounds of the remedial dental floss. Among these materials are numerous fluoride based compounds which can comprise inorganic fluoride salts such as soluble alkali metal, alkaline earth metal salts, and others. Examples of such include sodium fluoride, potassium fluoride, ammonium fluoride, a copper fluoride such as cuprous fluoride, zinc fluoride, sodium fluorosilicate, ammonium fluorosilicate, sodium fluorozirconate, barium fluoride, calcium fluoride, sodium monofluorophosphate, sodium silicofluoride, aluminum mono- and di-fluorophosphate, and fluorinated sodium calcium pyrophosphate. However, alkali metal and tin fluorides, such as sodium and stannous fluorides, sodium monofluorophosphate (MFP), amine fluoride, and mixtures thereof, are preferred.

The amount of fluorine based compound used is dependent to a large extent upon the type of fluorine compound, its solubility, and the formulation and structure of the final remedial dental floss used. As a result, substantial leeway is given to the quantities or amounts used and is only limited by any formulation or safety concerns.

Optimizing the effects and benefits of fluorides as well as other medicaments is also of prime importance and one way of accomplishing this is to provide as plaque free a dental enamel surface as possible. Most medicaments will, in general, tend to function better when given a cleaner dental surface on which to work. In this respect, the incorporation into the remedial dental floss of one or more peroxide based compounds, polishing or abrading agents, or other similar scrubbing or cleaning ingredients can render improved results for these substances tend to attack and remove plaques. As these plaques diminish the medicament's effect upon the teeth will be much more effective and useful.

Peroxide Compounds

The remedial dental floss may also make use of one or more peroxide based compounds such as, but not limited to, calcium peroxide, and sodium carbonate peroxide. Their use will help remove dental plaques and whiten teeth and so thereby reduce the incidence of dental caries and other related diseases. This ability to reduce dental decay stems from the fact that oxygen is released during their decompositions. Thus, when a peroxide based compound is utilized in the mouth the decomposal release of oxygen will vigorously attack all oral bacteria and plaques and also bleach or whiten teeth. Over time, as these plaques and their acidic byproducts are reduced the progression of carious lesions and that of calculus accumulation upon the teeth is also substantially curtailed.

Peroxide based compounds being mostly alkaline in nature will also facilitate the neutralization of oral acids. The level of alkalinity is not set at any specific figure or amount and thus can be suitably adapted to the remedial dental floss desired. The concentration of the peroxide based compound will also vary to some extent upon the type of peroxide compound employed and the final formulations used in the remedial dental floss. As a result, the amount employed is given extensive leeway in both use and concentration but both the quantity as well as the level of alkalinity must be of a safe level. Assimilating these peroxide compounds into the remedial dental floss can also be in a fashion similar to, but not limited to, that used by titanium dioxide.

Polishing or Abrading Agents

One or more polishing or abrading agents may also be utilized in the remedial dental floss. The type of abrading agents employed are not restricted to any specific types or quantities. This effectively allows the abrading compounds used to suit the final effects desired. In any case, their incorporation will help clean and polish teeth and so help produce a smooth and shiny dental surface that will resist discoloration, bacterial accumulation, and retention. Reducing plaques will also reduce the amount of oral acids and, in turn, dental demineralization. Moreover, as dental surfaces become cleaner the therapeutic performances of other ingredients such a fluorides will notably increase. Examples of polishing or abrading agents may include an oxide, dioxide, silicate, carbide, boride, carbonate, bicarbonate, phosphate, sulphide or nitride of such elements as calcium, magnesium, silicon, aluminum, iron, titanium, zinc, tungsten, zirconium, tin, sodium, potassium, and any mixtures thereof. Other compounds and mixtures are, of course, available.

While sodium bicarbonate is a mild abrading agent its usefulness does not end here. It can, for instance, also function as an anti-odorant and so provide some odour absorbing capabilities. Being a water soluble alkaline compound it also has the ability to neutralize some quantities of oral acids.

Sodium bicarbonate is also quite inexpensive and generally available in powdered form. Thus, it can be used to coat a remedial dental floss or it can be easily added, mixed, blended, or otherwise incorporated into the remedial dental floss in a fashion similar to, but not limited to, that used by titanium dioxide.

The amount of sodium bicarbonate used in the remedial dental floss may be adjusted to suite any specific taste, texture or structural feature. In some recipes it may even be desirable to omit its use altogether or conversely, the manufacturer may employ copious quantities to amplify its effects. The remedial dental floss may even comprise a suitable dental floss and titanium dioxide to which sodium bicarbonate is only added or it may include a sweetening or flavouring agent alone or in combination. As a result, the amount of sodium bicarbonate used is given great latitude and is, therefore, only limited by any formulation or safety concerns.

While sodium bicarbonate is a preferred compound there may be instances where it may be necessary or desirable to substitute one or more alternate compounds in place of sodium bicarbonate. Such times may arise when, for example, a formula for a remedial dental floss may conflict with sodium bicarbonate. Another example may result from the need to restrict high sodium diets. In any event, these substances, though less preferable than sodium bicarbonate, must also be water soluble and possess traits similar to those found in sodium bicarbonate. Such a compound may, therefore, include potassium bicarbonate. The exact solubility and alkalinity of potassium bicarbonate will vary from that provided by sodium bicarbonate but this can be compensated by varying the respective amount used in the remedial dental floss. Potassium bicarbonate can also be used alone or in combination with other ingredients as well as being blended or otherwise incorporated into the remedial dental floss in a fashion similar to or like that used with sodium bicarbonate.

Sweetening and Flavouring Agents

To foster greater consumer appeal the remedial dental floss may also contain one or more sweetening and or flavouring agents. Sweeteners include, for example, both natural and artificial compounds and combinations thereof in order to provide any sensorially acceptable blend. Examples of some common available sweeteners include sucrose, lactose, dextrose, maltose, dextrin, dried inverted sugar, fructose, levulose, galactose, corn syrup and their solids, sorbitol, mannitol, xylitol, hydrogenated starch hydrolysates, maltitol, sucralose, aspartame, salts of acesulfame, alitame, saccharin and its salts, cyclamic acid and its salts, glycyrrhizin, dihydrochalcones, thaumatin, monellin, and the like. Though any type of sweetener may be used artificial compounds are preferred for they reduce the potential for dental decay. Xylitol, an artificial sweetener, is particularly useful for it is incapable of nourishing bacteria and has demonstrated, in certain clinical studies, the ability to inhibit the growth of bacteria even in the presence of sugar.

The remedial dental floss may also utilize one or more flavouring agents. They may comprise essential oils, synthetic flavours, or mixtures thereof including, but not limited to, oils derived from plants and fruits such as citrus oils, fruit essences, mint, peppermint oil, spearmint oil, clove oil, oil of wintergreen, anise, sassafras, sage, eucalyptus, marjoram, cinnamon, lemon, orange, banana, cherry, apple, pineapple, grape, strawberry, blueberry, tutti frutti, methyl salicylate, and the like. Those skilled in the art will recognize that natural and artificial flavouring agents may be used independently or combined in any sensorially acceptable blend. All such flavours and flavour blends are contemplated by the present invention.

Addendum

The following references, the entire contents of which are hereby incorporated by reference into this specification, further elaborate and detail other ingredients, procedures, and information which may be of use in the disclosure herein.

(1) Accepted Dental Therapeutics, 39th Edition, Copyright 1982, by the American Dental Association, 211 E. Chicago Ave., Chicago, Ill., U.S.A., 60611 Library of Congress Number: 74[2]-MCAT (2) Comprehensive Dental Hygiene Care, 4th Edition, Written by: Irene R. Woodall, Copyright 1993, by Mosby-Year Book, Inc., 11830 Westline Industrial Drive, St. Louis, Mo., U.S.A., 63146. ISBN Number: 0-8016-7019-5

(3) Fenaroli's Handbook of Flavour Ingredients, Written by: Prof. Dr. Giovanni Fenaroli, Copyright 1971, by the Chemical Rubber Company, 18901 Cranwood Pkwy., Cleveland, Ohio, U.S.A., 44128. Library of Congress Number: 72-152143

(4) Flavor Technology, Profiles, Products, Applications, Written by: Henry B. Heath, M. B. E., B. Pharm.(London), Copyright 1978, Avi Publishing Company Incorporated, Westport, Conn., U.S.A. ISBN Number: 0-87005-258-9

Additional information regarding the subject of this invention can be found in the many books available to the public at libraries and technical centres or in the many patents and government publications currently available today.

In conclusion, therefore, the preceding description contains many specificities that should not be construed as limiting the scope of the invention but as merely providing illustrations of some of the presently preferred embodiments of this invention and thus, the scope of the invention should be determined by the appended claims and their legal equivalents rather than by the examples given.

The embodiments of the invention in which an exclusive property or privilege is claimed are defined as follows:

1. A remedial dental floss, used to whiten the enamel layer of the teeth, comprising a dental floss and particles of titanium dioxide, wherein some or all of said particles of titanium dioxide are of a size, sufficiently small, to be absorbed by said enamel layer of said teeth, and wherein the size of some or all of said particles of titanium dioxide are selected from the group consisting of:
   a. about 6.0 microns or less;
   b. about 1.5 microns or less;
   c. about 1.5 microns to about 0.1 microns;
   d. about 0.2 microns or less; and
   e. about 0.2 microns to about 0.1 microns.

2. The claim as recited in claim 1 wherein said dental floss is selected from the group consisting of:
   a. synthetic fibres, filaments or yarns;
   b. natural fibres, filaments or yarns;
   c. blends of synthetic-natural fibres, filaments or yarns;
   d. high or normal tenacity polymers, nylon, rayon, dacron, acrylic, acetate polymers, polypropylene, polyethylene, cotton, wool, silk, and linen, alone or in combination.

3. The claim as recited in claim 1 wherein said remedial dental floss further comprises at least one binder.

4. The claim as recited in claim 3 wherein said binder is selected from the group consisting of water soluble wax or wax-like compounds, non-water soluble wax or wax-like compounds, a polyethylene glycol wax, a microcrystalline wax, liquid polyethylene glycol esters of beeswax, and water soluble or non-water soluble polymers, soaps, gums, and resins.

5. The claim as recited in claim 3 wherein said remedial dental floss further includes at least one substance selected from the group consisting of pigmenting agents other than titanium dioxide, fluoride based compounds, peroxide based compounds, abrading agents, sweetening agents, flavouring agents, anti-odorants, alkaline agents, water, and mixtures thereof.

6. The claim as recited in claim 5 wherein said binder is selected from the group consisting of water soluble wax or wax-like compounds, non-water soluble wax or wax-like compounds, a polyethylene glycol wax, a microcrystalline wax, liquid polyethylene glycol esters of beeswax, and water soluble or non-water soluble polymers, soaps, gums, and resins.

7. The claim as recited in claim 6 wherein said substance is encapsulated or microcoated.

8. The claim as recited in claim 5 wherein said peroxide based compound is sodium carbonate peroxide, said abrading agent is sodium bicarbonate, and said sweetening agent is Xylitol.

9. The claim as recited in claim 8 wherein said substance is encapsulated or microcoated.

10. The claim as recited in claim 5 wherein said substance is encapsulated or microcoated.

11. The claim as recited in claim 3 wherein said remedial dental floss is made by incorporating titanium dioxide into at least one binder and applying the resultant mixture to said dental floss.

12. The claim as recited in claim 1 wherein said remedial dental floss further includes at least one substance selected from the group consisting of pigmenting agents other than titanium dioxide, fluoride based compounds, peroxide based compounds, abrading agents, sweetening agents, flavouring agents, anti-odorants, alkaline agents, water, and mixtures thereof.

13. The claim as recited in claim 12 wherein said peroxide based compound is sodium carbonate peroxide, said abrading agent is sodium bicarbonate, and said sweetening agent is Xylitol.

14. The claim as recited in claim 13 wherein said substance is encapsulated or microcoated.

15. The claim as recited in claim 12 wherein said substance is encapsulated or microcoated.

16. The claim as recited in claim 1 wherein said remedial dental floss is made by incorporating said particles of titanium dioxide into a liquid medium and applying the resultant mixture to said dental floss.

17. A method for reducing dental plaques and whitening the interproximal and subgingival areas of teeth comprising the following steps:

providing a dental floss;

providing particles of titanium dioxide, wherein some or all of said particles of titanium dioxide are of a size, sufficiently small, to be absorbed by the enamel layer of the teeth, and wherein the size of some or all of said particles of titanium dioxide are selected from the group consisting of:
  a. about 6.0 microns or less;
  b. about 1.5 microns or less;
  c. about 1.5 microns to about 0.1 microns;
  d. about 0.2 microns or less; and
  e. about 0.2 microns to about 0.1 microns;

contacting said particles of titanium dioxide with said dental floss by incorporating said particles of titanium dioxide therein or as a topical applicant in order to thereby produce a remedial dental floss; and flossing with said remedial dental floss to thereby reduce plaque, and permit the absorbtion of said particles of titanium dioxide by said enamel layer of said teeth and so thereby whiten said teeth.

18. The method of claim 17 including selecting said dental floss from the group consisting of:
  a. synthetic fibres, filaments or yarns;
  b. natural fibres, filaments or yarns;
  c. blends of synthetic-natural fibres, filaments or yarns;
  d. high or normal tenacity polymers, nylon, rayon, dacron, acrylic, acetate polymers, polypropylene, polyethylene, cotton, wool, silk, and linen, alone or in combination.

19. The method of claim 18 further including mixing at least one binder with said titanium dioxide particles prior to contacting with said dental floss.

20. The method of claim 19 wherein said medicated dental floss further includes at least one substance selected from the group consisting of fluoride based compounds, peroxide based compounds, abrading agents, pigmenting agents, sweetening agents, flavouring agents, anti-odorants, alkaline agents, water, and mixtures thereof.

* * * * *